(12) United States Patent
Kraus

(10) Patent No.: US 6,198,950 B1
(45) Date of Patent: Mar. 6, 2001

(54) METHOD FOR DETERMINING ANALYTES IN BODY FLUIDS AND ALSO A NEW IMPLANTABLE MEASUREMENT DEVICE

(75) Inventor: Michael Kraus, Vienna (AT)

(73) Assignee: Dade Behring Marburg GmbH, Marburg (DE)

(*) Notice: Subject to any disclaimer, the term of this patent is extended or adjusted under 35 U.S.C. 154(b) by 0 days.

(21) Appl. No.: 09/265,883

(22) Filed: Mar. 11, 1999

(30) Foreign Application Priority Data

Mar. 13, 1998 (DE) .............................. 198 11 017

(51) Int. Cl.[7] ...................................... A61B 5/00
(52) U.S. Cl. .................. 600/317; 600/341; 600/364; 128/903
(58) Field of Search ................... 600/309, 310, 600/317, 322, 341, 345, 352, 364; 128/903

(56) References Cited

U.S. PATENT DOCUMENTS

| | | | |
|---|---|---|---|
| 4,759,371 | * 7/1988 | Franetzki | 600/373 |
| 5,109,850 | * 5/1992 | Blanco et al. | 600/368 |
| 5,616,719 | * 4/1997 | Davalian et al. | 546/334 |
| 6,049,727 | * 4/2000 | Crothall | 600/310 |

FOREIGN PATENT DOCUMENTS 0 515 194 A2   11/1992   (EP) .

* cited by examiner

*Primary Examiner*—Eric F. Winakur
(74) *Attorney, Agent, or Firm*—Finnegan, Henderson, Farabow, Garrett and Dunner, L.L.P.

(57) ABSTRACT

The present invention relates to an implantable diagnostic apparatus for determining analytes in body fluids, which comprises a plurality of identical and/or different measurement units for determining an analytic parameter, in which a signal is generated which is specifically related to the variable to be determined and is transmitted by means of suitable measures to a receiver situated outside the body.

18 Claims, 4 Drawing Sheets

BRIEF DESCRIPTION OF THE DEVICE FOR IN VIVO DIAGNOSIS

BRIEF DESCRIPTION OF THE DEVICE FOR IN VIVO DIAGNOSIS

CROSS-SECTION THROUGH A MEASUREMENT CHAMBER

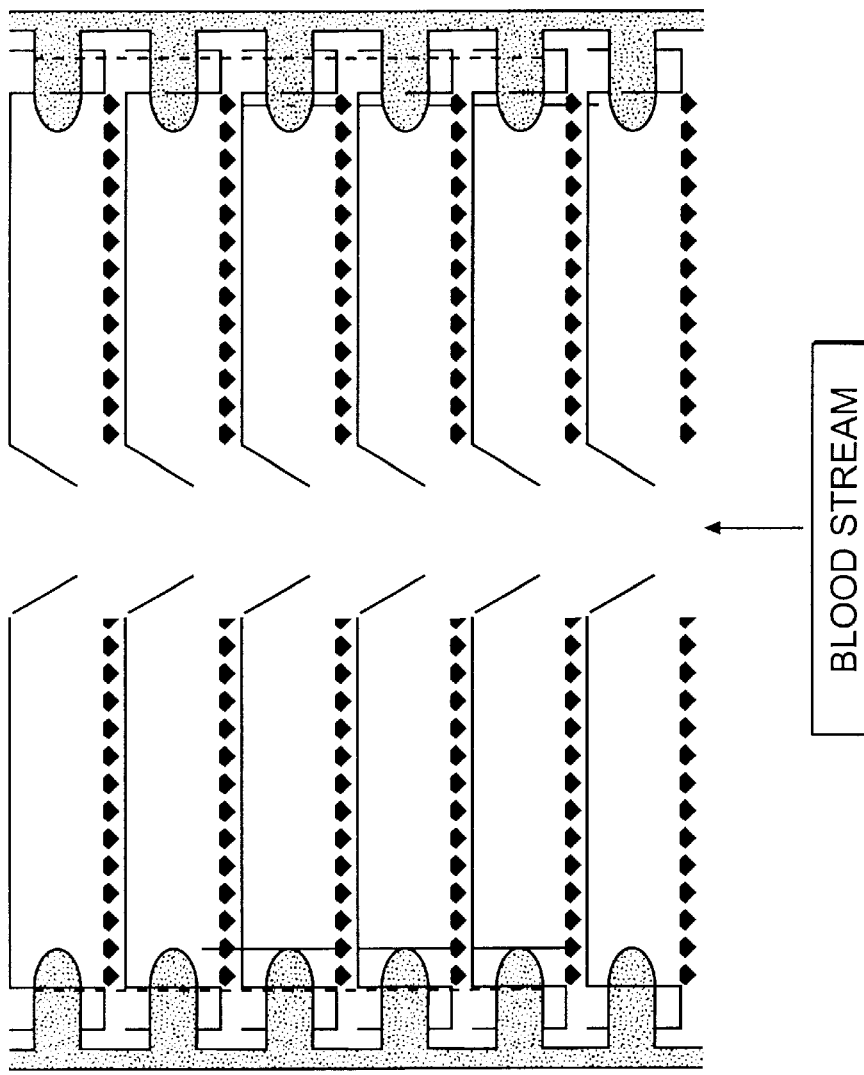
FIG. 2B CROSS-SECTION THROUGH THE MEASUREMENT DEVICE

METHOD FOR DETERMINING ANALYTES IN BODY FLUIDS AND ALSO A NEW IMPLANTABLE MEASUREMENT DEVICE

FIELD OF THE INVENTION

The present invention relates to implantable diagnostic apparatuses for determining analytes and methods for their use.

BACKGROUND

Implantable diagnostic apparatuses have already been described, for example, as parts of implantable insulin pumps. Such apparatuses essentially comprise an implantable measurement chamber in which a biosensor generates an analyte-dependent signal which, for its part, serves to control the insulin pump. These apparatuses have to be exchanged periodically when the insulin reserve is exhausted. Since this exchange takes place relatively frequently, the exchange interval is frequently shorter than the service life of the biosensors.

What is disadvantageous in the case of previous methods, and probably also a reason why the previous methods for glucose determination in connection with insulin pumps have not been applied to other parameters, is the problem that would arise if the biosensors are in contact with blood over a relatively long period of time and then their function is impaired, or even rendered impossible, by deposits such as, for example, fat- or protein-containing deposits (clots).

In particular, methods for determining coagulation parameters, which, by their nature, are often associated with clot formation, are not considered to be promising.

The object underlying the present invention is to provide an implantable diagnostic apparatus which enables the intervals between the exchanges of the apparatuses to be significantly lengthened and which allows the detection of coagulation and fibrinolysis parameters to determine hemostasis disturbances, e.g. by detecting factor VIII or measuring the PT (prothrombin) time.

It has been found, surprisingly, that the apparatus according to the invention, either as an individual measurement chamber or as an apparatus containing a plurality of measurement chambers, can advantageously be used to determine hemostasis disturbances, i.e. any malfunction of the hemostasis system.

SUMMARY OF THE INVENTION

The present invention relates to a diagnostic apparatus for determining analytes, which comprises at least (i) one measurement unit for single or continuous determination of an analyte, wherein the measurement unit generates a signal in the presence of the analyte to be determined; (ii) a signal transmission unit capable of converting that signal and capable of forwarding it to a signal-processing unit or forwarding the unconverted signal to a signal-processing unit; and (iii) a sample feeder to the measurement unit(s) which extends into the relevant liquid-containing body compartment, for instance a blood vessel. A light source which radiates a light suitable for exciting photosensitizers, preferably such as those as disclosed in EP-A2-0 515 194 (incorporated herein by reference), projects into the measurement chamber of said measurement unit. The surface within the measurement chamber shall be at least partly conductive or alternatively, the measurement chamber shall contain a light receiver. The measurement chamber preferably contains photosensitizers, especially photosensitizers incorporated into so-called sensitizer beads, capable of producing oxygen radicals after illumination. The analytes to be determined react with photosensitizers in such a way that the photosensitizers yield, depending on the analyte's concentration or activity, singlet oxygen which is measured by electrodes and converted into a transmittable signal. Alternatively, the signal is generated in the presence of analytes by photosensitizers that are in close proximity with acceptors, which might be incorporated into so-called acceptor beads, and the singlet oxygen generated by the photosensitizers activates said acceptors which subsequently produce light, and said light is detected. Acceptors preferably comprise substances such as described as a chemiluminescent compound in EP-A2-0 515 194.

The present invention relates fither to methods for determining analytes or their activity, preferably for the detection of hemostatsis disturbances, comprising an diagnostic apparatus as described above (i) wherein the analytes react with photosensitizers in such a way that the photosensitizers yield, depending on the analyte's concentration or activity, singlet oxygen which is measured by electrodes and converted into a transmittable signal; or (ii) wherein in the presence of analytes the signal is generated by photosensitizers that are in close proximity with acceptors and the singlet oxygen generated by the photosensitizers activates said acceptors which subsequently produce light, and said light is detected.

BRIEF DESCRIPTION OF THE DRAWINGS

FIG. 2B shows a cross-section through a measurement device comprising a multitude of measuring chambers which are connected with a blood stream.

DETAILED DESCRIPTION OF THE INVENTION

Figure 1:
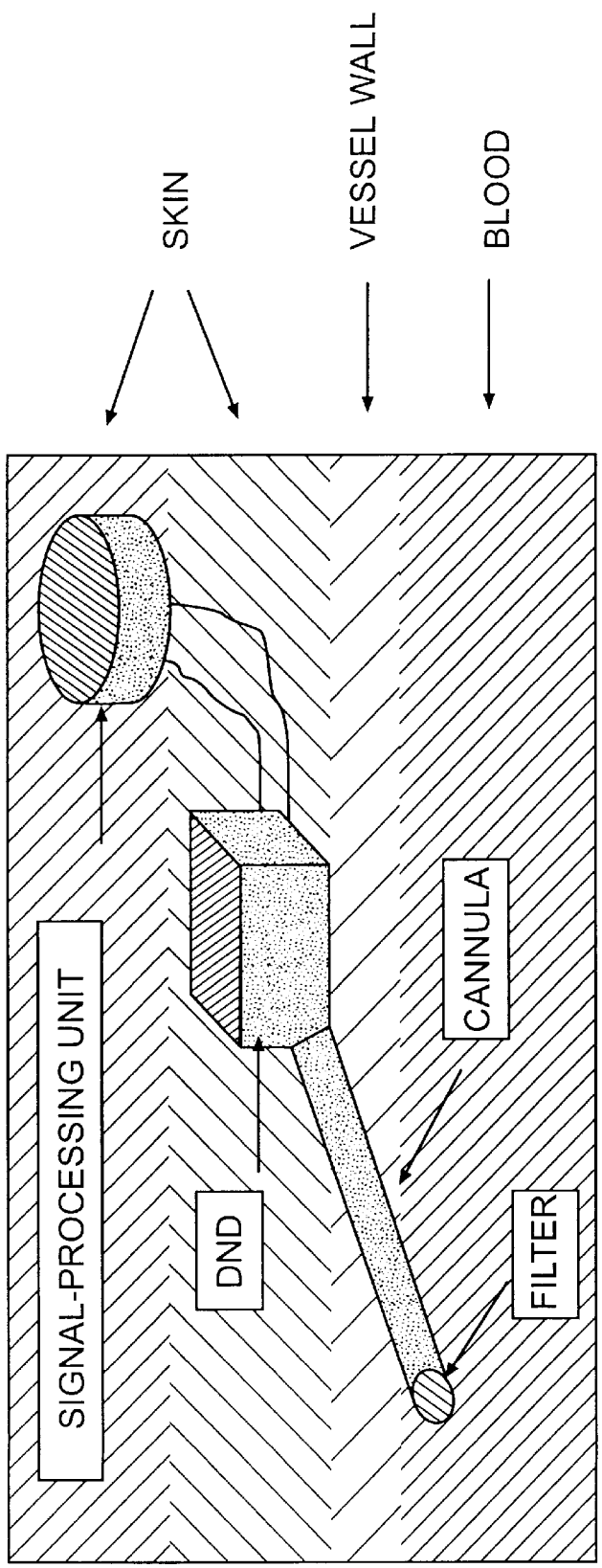
FIG. 1 shows the scheme of one preferred embodiment of such a diagnostic apparatus comprising a signal-processing unit and a diagnostic measurement device (DND) with a cannula, which is implanted under the skin in such a way that the cannula projects into a blood vessel. The cannula contains a filter which ensures that cellular constituents of the blood are excluded from the measurement chamber(s) within the DND, with the result that plasma is used in the analysis.

The present invention relates to a diagnostic apparatus for determining analytes, which comprises at least (i) one measurement unit for single or continuous determination of an analyte, wherein the measurement unit generates a signal in the presence of the analyte to be determined; (ii) a signal transmission unit capable of converting that signal and capable of forwarding it to a signal-processing unit or forwarding the unconverted signal to a signal-processing unit; and (iii) a sample feeder to the measurement unit(s) which extends into the relevant liquid-containing body compartment, for instance a blood vessel.

Determining analytes in the sense of the present invention means the detection of the analyte, measuring the analyte's concentration or its activity such as its enzymatic or binding activity. The analytes are the substances or compounds usually measured in a clinical laboratory to detect any diseases or to check a person's health (see also EP-A2-0 515 194), especially blood clotting factors and plasma proteins such as antibodies or peptide hormones.

In a preferred embodiment of the diagnostic apparatus, a light source which radiates a light suitable for exciting photosensitzers projects into the measurement chamber of said measurement unit, and the surface of the measurement chamber shall be at least partly conductive or, the measurement chamber shall comprise a light receiver. The measurement chamber preferably contains photosensitizers, preferably such as those as disclosed in EP-A2-0 515 194 and especially photosensitizers incorporated into so-called sensitizer beads, capable of producing oxygen radicals after illumination. The analytes to be determined react with photosensitizers in such a way that the photosensitizers yield, depending on the analyte's concentration or activity, singlet oxygen which is measured by electrodes and converted into a transmittable signal. Alternatively, the signal is generated in the presence of analytes by photosensitizers that are in close proximity with acceptors, which might be incorporated into so-called acceptor beads, and the singlet oxygen generated by the photosensitizers activates said acceptors which subsequently produce light, and said light is detected. Acceptors preferably comprise substances such as described as a chemiluminescent compound in EP-A2-0 515 194.

The diagnostic apparatus shall be implanted preferably outside a blood vessel. It shall usually not exceed an external dimension of 1500 μl, preferably of 500 μl, particularly preferably of 400 μl, especially preferably of 300 μl. The measurement unit of the diagnostic apparatus may be used only once or as long as its functionality is ensured. The diagnostic apparatus may comprise a plurality of measurement units, and is used for determining one single analyte or for determining different analytes. The energy necessary for signal generation and/or transmission is normally generated by a concomitantly implanted battery or is fed in by an external transducer.

The apparatus according to the invention comprises one or more measurement chambers which, in turn, essentially comprise three parts, to be precise the actual measurement chamber, a cannula which protrudes therefrom and, for its part, projects into a liquid-containing body compartment, such as a blood vessel, in whose fluid is the analyte to be determined. Furthermore, a signal transmission unit is associated with each measurement chamber—or else with all the measurement chambers together. The vessel end of the cannula may advantageously be closed off by a filter, which allows the passage of the analytes but excludes cells. The cannulae are furthermore provided with a closure flap which can be actuated by the action of an extracorporeal signal.

The diagnostic apparatus is advantageously additionally provided with an apparatus for storing the measurement signals, which can then be called up as required.

A preferred embodiment of the measurement chamber is illustrated in FIG. 2.

A plurality of said measurement chambers are advantageously combined to form a diagnostic apparatus, the number of individual measurement chambers preferably being from 20 to 50. The number as such is non-critical; if one determination per week is assumed, then a number of 50±10 appears to be particularly advantageous since one exchange per year is sufficient in this case.

Figure 2A:
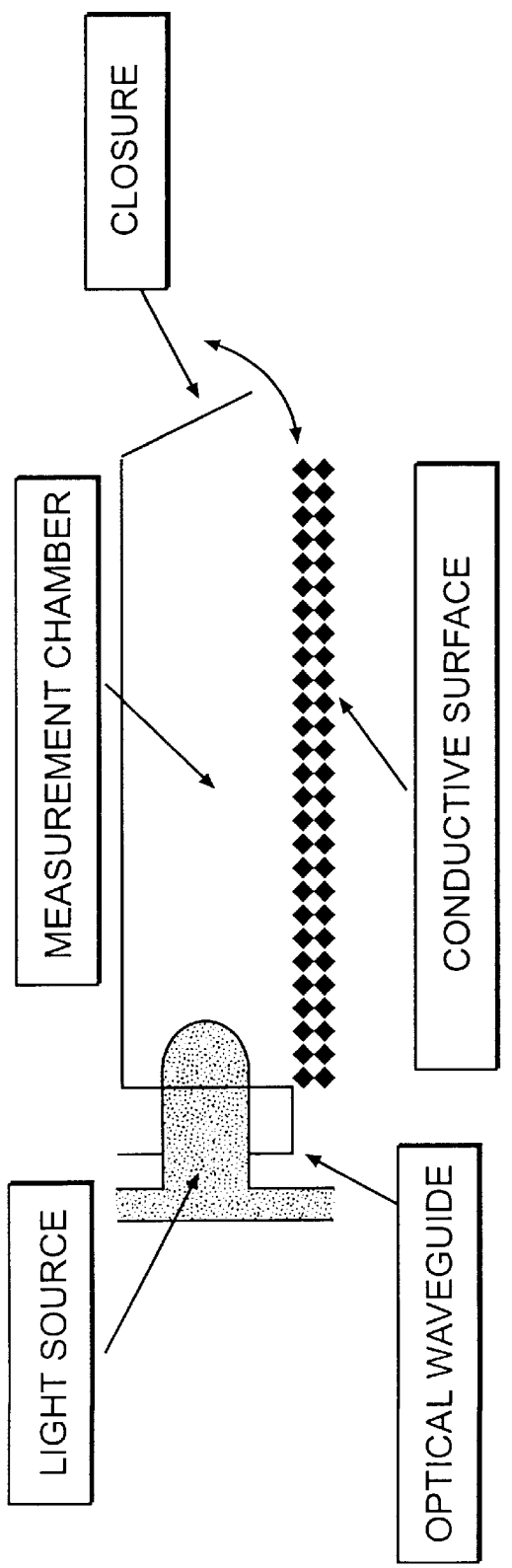
FIG. 2A shows the scheme of one embodiment of a measurement chamber: The interior of the measurement chamber can be illuminated directly by an light source, e.g. a small light-emitting diode, or indirectly via an optical waveguide. The measurement chamber can be closed or opened, e.g. by magnetically actuable closure flaps. At least a part of the surface of the measurement chamber is conductive.

The inventive method and device can be furished both for flow rate measurements and for individual determinations. The possibility of contactless signal transmission means that it can advantageously be used both for in- and outpatients, without additionally restricting the patients' mobility. The signal transmission methods are known per se to a person skilled in the art. The structure of one embodiment of the device is illustrated in FIG. 1. The structure of a specific measurement chamber is illustrated in FIG. 2A. The production of sufficiently small measurement chambers is possible by the methods which are known per se to a person skilled in the art.

The closure of the measurement chambers is especially important. Magnetically actuable closure flaps which can assume two fixed states (flip-flops) can advantageously be used here. FIG. 2B illustrates an arrangement of a plurality of measurement chambers. The supply of light to the individual measurement chambers can in this case be effected for example either via correspondingly small light sources, for example light-emitting diodes, arranged separately for each measurement chamber or via corresponding optical waveguides.

Each measurement chamber advantageously contains the reagent or reagents necessary for the reaction, for example, thromboplastin for a PT (prothrombin time) determination or antibodies or antigens for an immunochemcal reaction.

The present invention relates further to methods for determining analytes or their activity, preferably for the detection of hemostatsis disturbances, comprising an diagnostic apparatus as described above (i) wherein the analytes react with photosensitizers in such a way that the photosensitizers yield, depending on the analyte's concentration or activity, singlet oxygen which is measured by electrodes and converted into a transmittable signal; or (ii) wherein in the presence of analytes the signal is generated by photosensitizers that are in close proximity with acceptors and the singlet oxygen generated by the photosensitizers activates said acceptors which subsequently produce light, and said light is detected.

In a preferred embodiment of the invention, a coagulation process is initiated in the measurement unit and the course of the coagulation is determined by following a suitable parameter.

Figure 3:
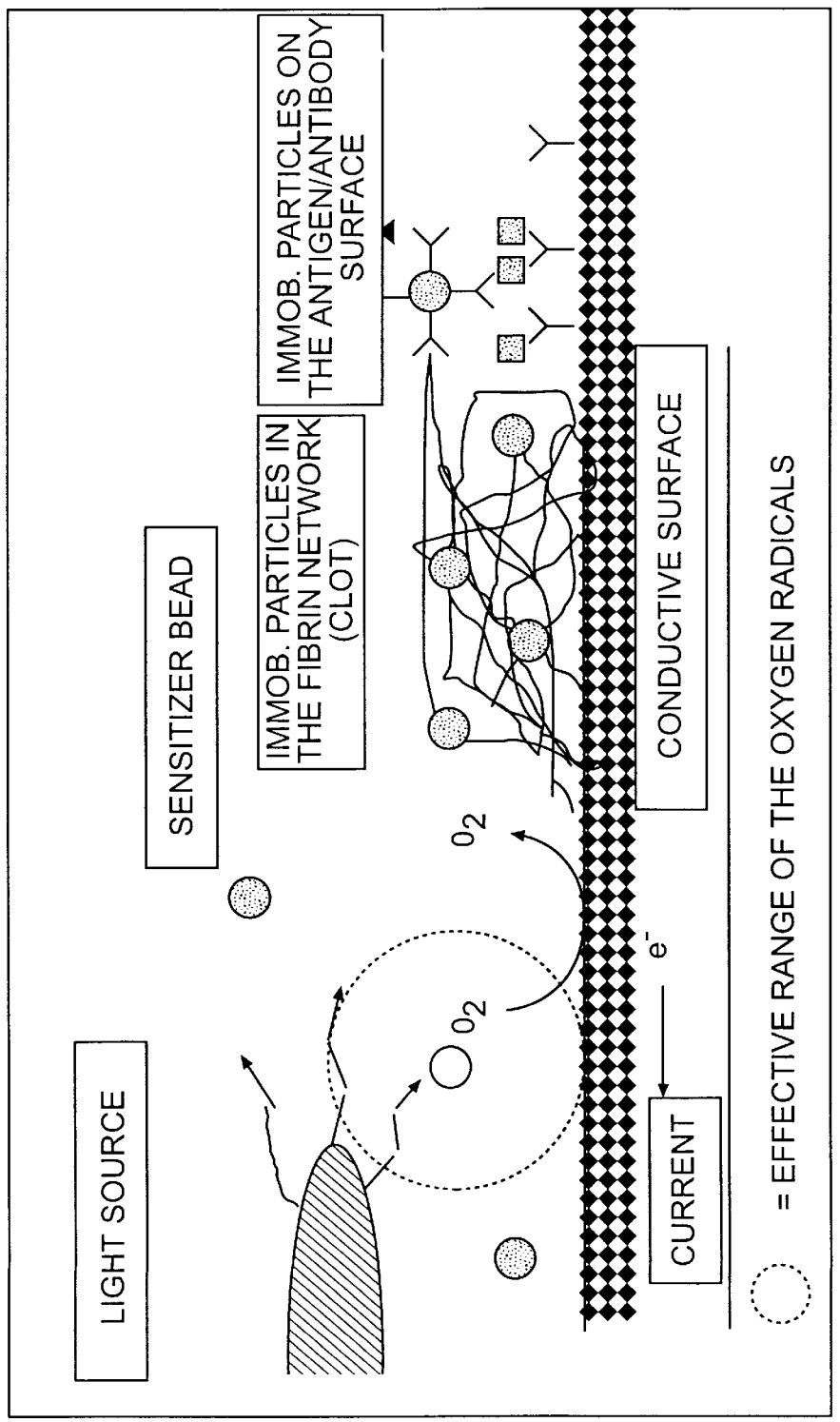
FIG. 3 illustrates a cross-section through the measurement chamber: Photosensitizers, preferably sensitizer beads, generating singlet oxygen on excitation, are applied, in the measurement chamber, together with analyte-specific reagents. A light source which radiates a light suitable for exciting the sensitizer beads projects into the measurement chamber. When coagulation takes place, the mobility of the sensitizer beads is altered by the fibrin network of the clot, and, as a result, sensitizer beads accumulate on the conductive surface. In the case of immunochemical reactions, corresponding binding partners such as antibodies are immobilized on the surface of the measurement chamber. As a result of the binding of the sensitizer beads to the analyte to be detected, which is bound to the binding partner of the surface, the sensitizer beads are brought into the vicinity of the conductive surface of the measuring chamber. Excitation of the sensitizer beads with light generates oxygen radicals which will generate a measurable signal if the conductive surface is within the effective range of the oxygen radicals. Due to the limited range in aqueous medium, only those oxygen radicals produced by sensitizer beads which are in close proximity to the conductive surface, e.g., by clot formation or by the immunochemical reaction, will reach the conductive surface and cause a measurable current flow.

The inventive technology is difficult to realize using the customary determination methods employed in coagulation. A new technology is advantageously employed, which new technology is described below:

Thus, for example, photosensitizers, preferably sensitizer beads generating singlet oxygen, which are described in EP-A2-0 515 194, for example, can be used. These sensitizer beads are applied, in the measurement chamber, to a conductive surface made of carbon, for example, together with the analyte-specific reagents. A light source which radiates a light suitable for exciting the sensitizer beads projects into the measurement chamber. When coagulation takes place, the mobility of the sensitizer beads is altered, as a rule restricted, and, as a result, sensitizer beads accumulate on the conductive surface and a measurable current flow is produced (also see FIG. 3).

An analogous method can be employed for immunological determinations, where a specific binding partner is immobilized on the conductive surface and sensitizer beads which are likewise coated with a binding partner specific to the analyte are bound by the analyte in the vicinity of the conductive surface, which again leads to a measurable change in the current flow.

An advantageous embodiment can be designed as follows:

A device comprising the elements of a measurement unit, a signal-processing unit and also a cannula is implanted under the skin, with the result that the cannula projects into a vessel. The units are produced by means of microtechnology of the kind used for example in the fabrication of integrated circuits (chip technology) and, as a result, are small enough that they can be implanted using known endoscopic techniques. For the measurement, an external receiver is emplaced and the current for the measurement is transmitted conductively. At the same time, the measurement signals or results are transmitted to the receiver, where they can be interrogated.

The measurement unit comprises discrete measurement chambers which can be individually closed off by valves and can be used just once, and also a pump apparatus connected to the cannula, and also, if appropriate, to a supply reservoir containing physiological NaCl for flushing the cannula. Furthermore, the measurement unit contains a light generator, for instance a microlaser, and also current lines for deriving and processing the measurement signal. The measurement chamber contains a miniaturized diode or is connected to the central light generator via an optical waveguide. The measurement chamber contains the reagents which are necessary for detecting the plasma protein or for the coagulation analysis. The methods for producing the discrete components, such as valves or pumps, for example, are known per se to a person skilled in the art.

The detection of the reaction is carried out by means of a novel combination of sensitizer beads with an amperometrically sensitive printed circuit board. Excitation with light generates oxygen radicals which generate a measurable signal on the printed circuit board. In the event of clot formation, said radicals are preferably produced in the vicinity of the printed circuit board, on account of the immobilization. The free solution can be kept in motion by stirrers. In the case of immunochemical reactions, corresponding binding partners are immobilized on the surface. As a result of the binding of the sensitizer beads to the analyte to be detected, which is bound to the binding partner of the surface, the sensitizer beads are brought into the vicinity of the printed circuit board, thereby transferring a charge (oxygen radicals) to the printed circuit. The measurement signal is thus proportional to the analyte concentration. As an alternative, it is also possible to use such reagents as described in EP-A2-0 515 194, comprising sensitizer and acceptor beads. The measurement chamber would then contain a light receiver instead of a printed circuit board.

The signal-processing unit contains a computing processor and also a transducer for transmission of the results, and also further electrical units for receiving energy.

The cannula may contain filters which ensure that cellular constituents of the body liquids are excluded, with the result that in case of blood as the body liquid, plasma is used in the analysis. After the measurement, access ducts, cannula and filter can be cleaned by backward flushing with physiological sodium chloride solution.

What is claimed is:

1. A diagnostic apparatus for determining analytes in body liquids, which comprises
   (i) at least one measurement unit for single or continuous determination of an analyte, wherein the measurement unit contains at least one measurement chamber and generates a signal in the presence of the analyte to be determined and wherein the measurement chamber(s) contain(s) photosensitizers;
   (ii) at least one signal transmission unit capable of converting the signal and forwarding it to a signal-processing unit or capable of forwarding the unconverted signal to a signal-processing unit; and
   (iii) at least one sample feeder to each measurement unit which is adapted to extend into the relevant liquid-containing body compartment.

2. The apparatus as claimed in claim 1, wherein a light source which radiates a light suitable for exciting photosensitizers projects into at least one measurement chamber of said measurement unit(s).

3. The apparatus as claimed in claim 1 or 2, wherein a surface within the measurement chamber(s) of said measurement unit(s) is/are at least partly conductive.

4. The apparatus as claimed in claim 3, wherein the analytes react with photosensitizers in such a way that the photosensitizers yield, depending on the analyte's concentration or activity, singlet oxygen, wherein said singlet oxygen is measured by electrodes and converted into a transmittable signal.

5. The apparatus as claimed in claim 1, wherein the measurement chamber(s) contain(s) photosensitizers capable of producing oxygen radicals after illumination.

6. The apparatus as claimed in claim 5, wherein the photosensitizers are sensitizer beads.

7. The apparatus as claimed in claim 1, wherein the liquid-containing body compartment is a blood vessel.

8. The apparatus as claimed in claim 1, wherein the measurement unit(s) is/are adapted to be implanted outside of a blood vessel.

9. The apparatus as claimed in claim 1, wherein said apparatus does not exceed an external volume of 1500 $\mu$l.

10. The apparatus as claimed in claim 1, wherein the apparatus comprises a plurality of measurement units, and which is adapted for use in determining one single analyte.

11. The apparatus as claimed in claim 1, wherein the apparatus comprises a plurality of measurement units, and which is adapted for use in determining different analytes.

12. The apparatus as claimed in claim 1, wherein the energy necessary for at least one of either signal generation or transmission is generated by a concomitantly implanted battery.

13. The apparatus as claimed in claim 1, wherein the energy necessary for at least one of either signal generation or transmission is fed in by an external transducer.

14. The apparatus as claimed in claim 4, wherein in the presence of analytes the signal is generated by photosensitizers that are in close proximity with acceptors and the singlet oxygen generated by the photosensitizers activates said acceptors which subsequently produce light, and said light is detected.

15. The apparatus as claimed in claim 14, wherein the acceptors are acceptor beads.

16. Method for determining analytes or their activity using an apparatus as claimed in claim 1, the method comprising the steps if:
   (a) reacting the analytes with photosensitizers in such a way that the photosensitizers yield, depending on the analyte's concentration or activity, singlet oxygen;
   (b) measuring said singlet oxygen;
   (c and converting said measurements into a transmittable signal.

17. A method for determining analytes or their activity using a diagnostic apparatus as claimed in claim 1, the method comprising the steps of:
   (a) generating a signal in the presence of analytes with photosensitizers that are in close proximity with acceptors;
   (b) activating said acceptors with singlet oxygen generated by said photosensitizers which subsequently produce light;
   (c) and detecting said light.

18. A method according to claims 16 or 17 used for the detection of hemostasis disturbances.

* * * * *